Nov. 30, 1954 F. W. ANDERSON Plant Pat. 1,327
NECTARINE TREE
Filed March 29, 1954
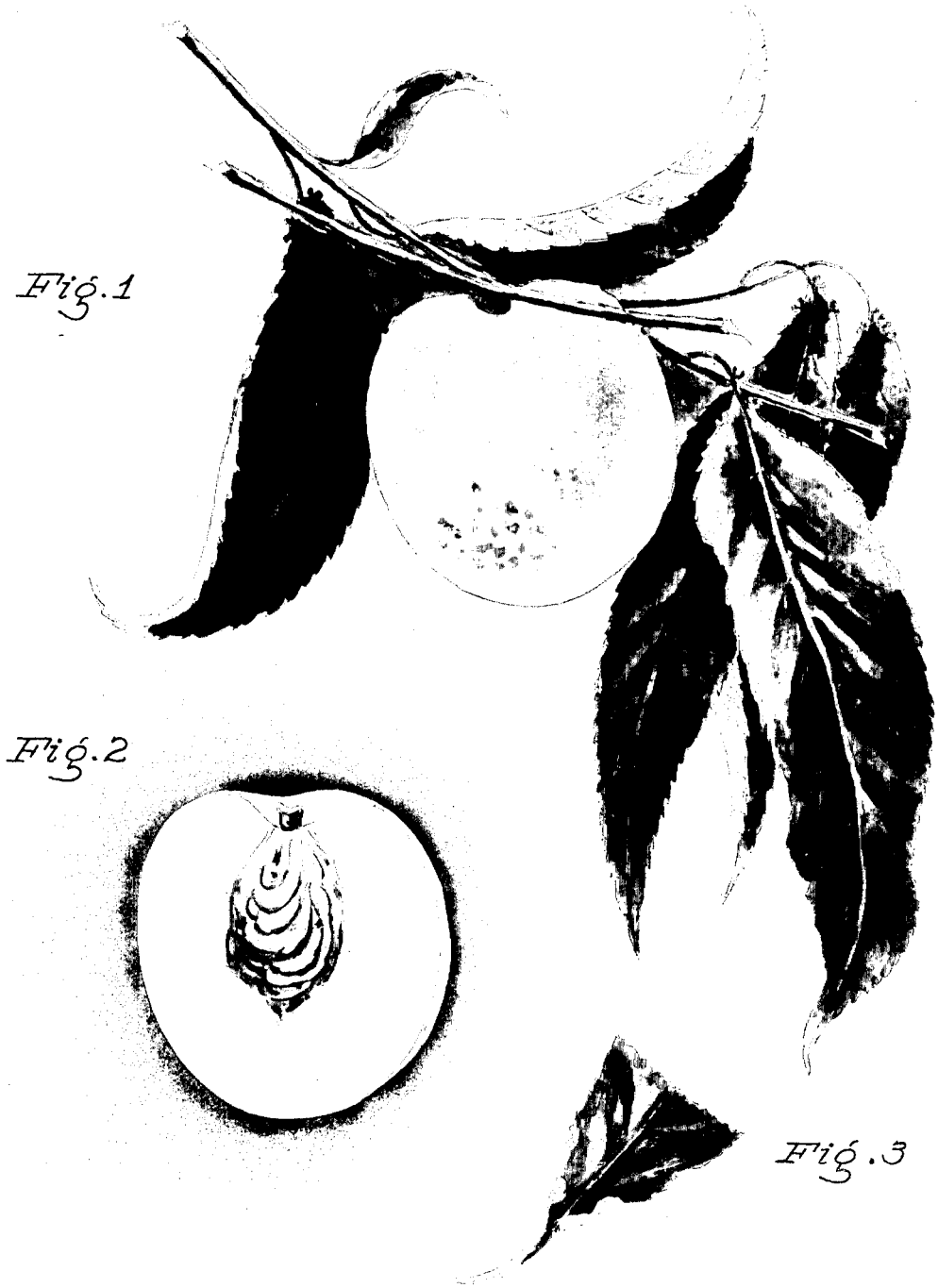
WITNESS
Addison J. Avery
INVENTOR
Frederic W. Anderson
Webster & Webster
ATTYS.

United States Patent Office

Plant Pat. 1,327

Patented Nov. 30, 1954

1,327

NECTARINE TREE

Frederic W. Anderson, Merced, Calif.

Application March 29, 1954, Serial No. 419,632

1 Claim. (Cl. 47—62)

This invention is directed to a new and distinct variety of nectarine tree which bears yellow fleshed, freestone fruit, highly attractive in appearance; the variety having been originated by me as an F-1 seedling of a cross between Le Grand nectarine (United States Plant Patent No. 549) and Gold Nugget nectarine (United States Plant Patent No. 1249).

The instant variety of nectarine tree is characterized—as to novelty—by yellow fleshed freestone fruit having a ripening period in which there has not heretofore been a commercially desirable nectarine; to-wit, in the period between the white fleshed John Rivers and Gower nectarines (both unpatented), and between the yellow fleshed Gold Nugget and Sun Grand varieties of nectarines.

The Sun Grand nectarine is the subject of United States Plant Patent No. 974.

The John Rivers nectarine and the Gower nectarine ripen approximately forty days and fourteen days, respectively, before the Elberta peach (unpatented), whereas the present variety of nectarine ripens approximately twenty-eight days before the Elberta peach; thus filling a gap in which a commercially desirable nectarine finds demand in the trade.

In further comparison to the John Rivers and Gower nectarines the fruit of the present variety will average 50% larger; the shipping and keeping qualities being much better than the John Rivers, and approximately equal to those of the Gower.

As compared with the Gold Nugget nectarine the fruit of the present variety ripens about a week later and averages 25% larger, and—in comparison to the Sun Grand—such fruit ripens about a week earlier, averaging only slightly larger in size, and being not quite as firm fleshed.

A further distinguishing characteristic of the present variety of nectarine is that it has stems which are quite stout, adhering well to the stone.

The present new and distinct variety of nectarine was originated in my experimental orchard near Merced, California, during the course of a long and continuing nectarine improvement program; such origination having been accomplished in the following manner:

All of the blossoms on a Le Grand nectarine tree were emasculated and the stigmas of the remaining pistils were pollinated from the flowers of a Gold Nugget nectarine tree. The seeds from the resultant fruit were then planted in a nursery row, and after they had grown to a height of about eighteen inches the seedlings were top-worked in orchard trees. Subsequently, such top workings were carefully observed. Of such top workings one was recognized by me as having a ripening period which filled a gap in the ripening period between certain other commercial or shipping varieties of nectarines; i. e., between the white fleshed John Rivers and Gower nectarines, and between the yellow fleshed Gold Nugget and Sun Grand nectarines, as aforesaid.

Subsequent asexual reproductions of the variety, by top working in mature trees in my orchard located as aforesaid, evidenced the fact that the present variety runs true in all respects.

In the drawings:

Fig. 1 is an elevation showing one of the fruit of the present variety, together with twigs and leaves.

Fig. 2 is a sectional elevation of one of the fruit with the stone exposed.

Fig. 3 is a fragmentary elevation of one of the leaves.

Referring now more specifically to the pomological details of this new and distinct variety of nectarine tree, the following is an outline description thereof; all major color plate identifications being by reference to Maerz and Paul Dictionary of Color:

Tree: Large; vigorous; spreading; open. Very productive. Regular bearer.

Trunk: Medium stocky. Medium texture.

Branches: Medium stocky. Medium texture. Brown.

Leaves: Medium sized, averaging 6⅜" in length and 1½" in width. Medium thickness.

*Color.*—Top side—medium green (21-L-7 shading to 22-L-8). Under side—lighter green (21-L-4).

*Margin.*—Crenate.

*Pistil.*—Medium length. Medium thickness.

*Glands.*—Average two on petiole; two to three on blade. Alternate. Medium size. Reniform. Stipules—none.

Flowers: Medium; non-showy; pink. Time of bloom—medium, usually two or three days after the Elberta peach.

Fruit:

*Maturity when described.*—Eating—ripe. First picking July 2, 1953; last picking July 12, 1953.

*Size.*—Large; uniform. Average in axial diameter—2¾". Average transversely in suture plane—2⅝".

*Form.*—Uniform; symmetrical; globose.

*Suture.*—Distinct.

*Ventral surface.*—Rounded slightly. Lips equal.

*Cavity.*—Rounded. Average depth—⅝". Average breadth—⅞". Markings—red.

*Base.*—Round.

*Apex.*—Short; rounded.

*Stem.*—Stout. Adheres well to stone.

Skin: Medium thickness. Medium toughness. No tendency to growth cracks.

*Down.*—Wanting.

*Color.*—Yellow (10-L-6 shading into 11-L-11), overlaid to a substantial extent with red (3-L-10 shading into 6-L-6), mottled with red (4-K-12).

Flesh:

*Amygdalin.*—Moderate.

*Juice.*—Abundant; rich.

*Texture.*—Firm; fine; tender; meaty.

*Ripens.*—Even.

*Flavor.*—Sub-acid.

*Aroma.*—Not very pronounced.

*Eating quality.*—Good to best.

*Color.*—Yellow (9-J-5), with reddish tinge next to stone.

Stone: Free.

*Size*—Medium. Average length—1⅝". Average breadth—1⅛". Average thickness—⅞".

*Form.*—Oval.

*Base.*—Oblique.

*Hilum.*—Broad; oval.

*Apex.*—Acute.

*Sides.*—Equal.

*Surface.*—Irregularly furrowed and pitted throughout.

*Pits.*—Elongated.

*Ventral edge.*—Thin.

*Dorsal edge.*—Full, with narrow groove to above center.

*Ridges.*—Continuous.

*Kernel.*—Bitter.

*Tendency to split.*—Slight.

*Color.*—Brown (7-L-12) shading to a reddish purple (47-L-1) in the direction of the base end.

Use: Market; dessert; local; shipping.

Keeping quality: Good.

Shipping quality: Good.

Resistance to disease: No unusual susceptibility noted, and the usual spray practices have maintained under control those insects and diseases that are prevalent in the orchard areas of California.

The tree and its fruit herein described may vary in slight detail due to climatic and soil conditions under which the variety may be grown.

Having thus described my invention, I claim:

A new and distinct variety of nectarine tree, as described and illustrated, characterized—as compared to the John Rivers and Gower nectarines—by freestone fruit which is yellow instead of white fleshed, averaging approximately 50% larger and ripening in a period between the harvest thereof, of better keeping and shipping quality than said John Rivers nectarine and comparable to the Gower nectarine; and additionally characterized—as compared to the Gold Nugget and Sun Grand nectarines by a ripening period of approximately a week later and a week earlier, respectively, than the harvest of the same, averaging approximately 25% larger than the fruit of the Gold Nugget nectarine, and slightly larger than the Sun Grand nectarine; and further characterized by stout stems which adhere well to the stone.

No references cited.